(12) United States Patent
Sugahara (10) Patent No.: US 9,708,364 B2
(45) Date of Patent: Jul. 18, 2017

(54) METHOD FOR FORMING PROTEIN CRYSTAL

(75) Inventor: Michihiro Sugahara, Sayo-cho (JP)

(73) Assignee: RIKEN, Wako-shi (JP)

( * ) Notice: Subject to any disclaimer, the term of this patent is extended or adjusted under 35 U.S.C. 154(b) by 0 days.

(21) Appl. No.: 13/474,984

(22) Filed: May 18, 2012

(65) Prior Publication Data
US 2013/0196160 A1 Aug. 1, 2013

(30) Foreign Application Priority Data
May 18, 2011 (JP) .................................. 2011-111682

(51) Int. Cl.
*C07K 1/30* (2006.01)
*B65B 5/04* (2006.01)
*G01N 23/207* (2006.01)

(52) U.S. Cl.
CPC .............. *C07K 1/306* (2013.01); *B65B 5/04* (2013.01); *G01N 23/207* (2013.01); *Y10T 428/2991* (2015.01)

(58) Field of Classification Search
None
See application file for complete search history.

(56) References Cited

U.S. PATENT DOCUMENTS

2006/0081173 A1* 4/2006 Yoshizaki ................ C30B 7/14
117/200
2007/0191590 A1* 8/2007 Visuri et al. .................. 530/344

FOREIGN PATENT DOCUMENTS

JP 2007-055931 A 3/2007
JP 2007-230841 A 9/2007
WO 2009/091053 A1 7/2009

OTHER PUBLICATIONS

Hampton Research (http://hamptonresearch.com/documents/growth_101/6.pdf (2001)).*
Lin et al (Physically crosslinked alginate/N,O-carboxymethyl chitosan hydrogels with calcium for oral delivery of protein drugs. Biomaterials. vol. 26, Issue 14, May 2005, pp. 2105-2113).*
Kim et al (Release of albumin from chitosan-coated pectin beads in vitro. International Journal of Pharmaceutics. vol. 250, Issue 2, Jan. 16, 2003, pp. 371-383).*
Sugiyama et al, "Growth of Protein Crystals in Hydrogels Prevents Osmotic Shock", Journal of the American Chemistry Society, vol. 134, pp. 5786-5789, Mar. 21, 2012.
R. Willaert et al., "Protein crystallization in hydrogel beads", Acta Crystallographica Section D, Biological Crystallography, research papers, D.61, (2005), pp. 1280-1288.
Chayen et al, "Microbatch crystallization under oil—a new technique allowing many small-volume crystallization trials", Journal of Crystal Growth,vol.122, pp. 176-180,1992.
Sugawara et al, "Protein crystallization in polymer capsules", Seikagaku, vol. 83, No. 8. 2011. See machine translation of Japanese Office Action dated Mar. 29, 2016 for concise statement of relevance.
Office Action dated Mar. 29, 2016, issued in counterpart Japanese Patent Application No. 2012-107521, with machine translation. (9 pages).

* cited by examiner

*Primary Examiner* — Jake Vu
(74) *Attorney, Agent, or Firm* — Westerman, Hattori, Daniels & Adrian, LLP (57) ABSTRACT

A method for producing a capsule for protein crystallization is provided. The method comprises adding a solution containing a protein and a gelling agent to an ionic cross-linking solution to form an ionically cross-linked gel capsule that encapsulates a solution of the protein.

8 Claims, 6 Drawing Sheets
(6 of 6 Drawing Sheet(s) Filed in Color)

METHOD FOR FORMING PROTEIN CRYSTAL

CROSS-REFERENCE TO RELATED APPLICATION

This application claims the benefit of Japanese Patent Application No. 2011-111682, filed May 18, 2011, which is incorporated herein by reference in its entirety.

TECHNICAL FIELD

The present invention relates to a method for producing a protein crystal, a composition for protein crystallization, a kit for producing a capsule for protein crystallization, a method for producing a protein crystal, a plate for protein crystallization, a composition of a protein crystal, and a method for analyzing protein crystal structure.

A protein crystal obtained by the present invention can be used for a protein crystal sample to be applied for X-ray crystal structural analysis.

BACKGROUND

In recent structural biology, techniques for analyzing the conformation of a protein using NMR or an electron microscope have been developed dramatically. Among them, X-ray crystal structural analysis is the most suitable technique for revealing the conformation at atomic resolution, provided that a high-quality protein crystal is obtained. In the world's largest synchrotron radiation facility, SPring-8, a microfocus beamline has newly begun to operate, in addition to an optimized RIKEN beamline for structural biology. This is making it possible to collect diffraction data of microcrystals, which were difficult to measure heretofore. For example, Japanese Laid-open Patent Publication No. 2007-055931 and Japanese Laid-open Patent Publication No. 2007-230841 disclose methods for crystallizing a protein.

In conventional development of techniques for protein crystallization, large-scale screening of crystallization conditions, micro-dispensation of a sample at the nanoscale, and a protein crystallization apparatus that enables further rapid setup of crystallization have been mainly developed, based on crystallization methods such as a hanging drop method, a sitting drop vapor diffusion method, and an oil microbatch method. As a result, many conformations of proteins have been determined.

However, there is a problem that a high-quality protein crystal is still difficult to obtain even with the conventional techniques.

SUMMARY OF THE INVENTION

The present inventor focused on the fact that the problem of difficulty in obtaining a high-quality protein crystal is attributed to the spoilage of the high-quality protein resulting from damage to the protein crystal due to direct contact of a mounting device or the like with the protein crystal when the crystallized protein is taken out for X-ray crystal structural diffraction.

An object of the present invention is to provide a new crystallization technique that enables a protein crystal to be easily taken out and handled without directly damaging the protein crystal. The present inventor developed a technique for crystallization in a capsule of polymer gel by ionic cross-linkage.

In a first aspect of the present invention, a method for producing a capsule for protein crystallization is provided. The method comprises adding a solution containing a protein and a gelling agent to an ionic cross-linking solution to form an ionically cross-linked gel capsule that encapsulates a solution of the protein.

In a second aspect of the present invention, a composition for protein crystallization is provided. The composition comprises a shell including an ionically cross-linked gel, wherein the shell encapsulates a solution including a protein.

In a third aspect of the present invention, a kit for producing a capsule for protein crystallization is provided. The kit comprises a gelling agent and an ionic cross-linking solution.

In a fourth aspect of the present invention, a method for producing a protein crystal is provided. The method comprises:

(a) adding a solution containing a protein and a gelling agent to an ionic cross-linking solution to form an ionically cross-linked gel capsule; and (b) maintaining the capsule formed in step (a) in a crystallization solution.

In a fifth aspect of the present invention, a method for producing a protein crystal is provided. The method comprises:

(a) providing a plate for protein crystallization, wherein the plate has one or more wells, a crystallization solution and a non-volatile oil covering the crystallization solution are placed in each well, and the crystallization solution is an ionic cross-linking solution; and (b) adding a solution containing a protein and a gelling agent to the non-volatile oil to form and maintain an ionically cross-linked gel capsule in the crystallization solution.

In a sixth aspect of the present invention, a plate for protein crystallization is provided. The plate has a plurality of wells, wherein a crystallization solution containing one or more divalent or higher-valent metal cations, and a non-volatile oil covering the crystallization solution are placed in each well.

In a seventh aspect of the present invention, a composition of a protein crystal comprising a shell including an ionically cross-linked gel capsule is provided. The shell encapsulates a protein crystal.

In an eighth aspect of the present invention, a method for analyzing protein crystal structure is provided. The method comprises subjecting an ionically cross-linked gel capsule encapsulating a protein crystal to protein structural analysis.

In a ninth aspect of the present invention, a method for storing a capsule for protein crystallization is provided. The method comprises storing an ionically cross-linked gel capsule encapsulating a protein crystal in liquid nitrogen in a container.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 5 shows photographs depicting protein crystallized in the capsules, (a-k) 1.0 μl dispensation: (A) a photograph taken immediately after the dispensation: the solution becomes clear toward the center as ionic cross-linkage proceeds; (B) a crystal of lysozyme: Reagent No. 49 was used as the crystallization reagent; (C) a crystal of lysozyme: Reagent No. 60 was used; (D) a crystal of glucose isomerase: Reagent No. 23 was used; (E) a crystal of glucose isomerase: Reagent No. 28 was used; (F) a crystal of xylanase: Reagent No. 63 was used; (G) a crystal of catalase: Reagent No. 24 was used; (H) a crystal of protein ID00367: Reagent No. 57 was used; (I) a crystal of protein ID00403: Reagent No. 64 was used; (J) a crystal of protein ID70067: Reagent No.; (K, L) crystals of lysozyme obtained by crystallization with 0.5 μl-dispensation: Reagent No. 49(K) and No. 60(L) were used.

DETAILED DESCRIPTION OF THE PREFERRED EMBODIMENTS

The present invention provides a method for producing a capsule for protein crystallization, comprising adding a solution containing a protein and a gelling agent to an ionic cross-linking solution to form an ionically cross-linked gel capsule that encapsulates a solution of the protein.

The present invention also provides a kit used for the above method, a composition produced by the above method, a method for producing a protein crystal, a composition of a protein crystal, and a method for analyzing protein crystal structure.

As used herein, an ionically cross-linked gel refers to a gel formed from a cross-linked structure of a cation and an anion. For example, it is known that addition of one or more divalent or higher-valent metal cations, such as calcium ion ($Ca^{2+}$), cobalt ion ($Co^{2+}$), or cadmium ion ($Cd^{2+}$), to an aqueous solution of polysaccharide and/or a salt of polysaccharide gives a cross-linked structure (egg-box structure) by ion exchange to form a gel.

An ionically cross-linked gel capsule refers to a particle produced by mixing a gelling agent and an ionic cross-linking solution.

As used herein, "encapsulate" means that a protein solution or a protein crystal is contained within a shell of the ionically cross-linked gel capsule. A protein or a crystal of a protein is present in a fluid containing a gelling agent. Although it depends on the concentration, such a fluid is viscous, and the convection is suppressed. Thus, the fluid provides a favorable environment for crystallization and growth of the crystal.

The gelling agent includes an anionic polymer. In the present invention, any gelling agent that forms an ionic cross-linkage may be used. Examples of the gelling agent include low-methoxy pectin, alkali metal (Li, Na, K) salts of alginic acid such as sodium alginate, polysaccharides and/or salts of polysaccharides such as gellan gum and ι carrageenan. Sodium alginate is preferred. Since these gelling agents are also anionic polymers, they may be also herein referred to as anionic polymers. The concentration of the gelling agent is from about 0.05 to about 5 wt %, preferably about 0.1 to about 1 wt %.

The ionic cross-linking solution contains a cationic substance that forms an ionically cross-linked gel in the presence of the gelling agent. Examples of such substances include calcium. When calcium is used, the concentration of calcium in the solution is about 0.1 to about 0.5 M, preferably about 0.2 to about 0.3 M. When the concentration of calcium is too low, gelation does not occur, or it takes time for gelation. In such case, the resultant gel may have insufficient strength, such that the protein may leak out of the gel. When the concentration of calcium is too high, it may cause an adverse effect on the protein crystal formation. Here, regarding calcium, calcium salts having high solubility in water, such as calcium chloride, calcium bromide, calcium iodide, calcium nitrate, calcium perchlorate, calcium lactate, and calcium gluconate, may be used.

In one embodiment, an alkali metal salt of alginic acid is used as the gelling agent and a solution containing a calcium ion is used as the ionic cross-linking solution to form a gel of calcium alginate as the ionically cross-linked gel.

As for the protein, any soluble protein that is desired to be crystallized may be used. For example, the protein may be an enzyme (e.g., hydrolase, isomerase, lyase, ligase, transferase, or oxidoreductase), a receptor, hormone, cytokine, antibody, or a transcription factor, but the protein is not limited thereto as long as it is a protein.

The concentration of the protein to be crystallized is preferably as high as possible for crystallization. Accordingly, the protein is dissolved at a high concentration that allows dissolution in the gelling agent. The concentration of the protein is, for example, 1 to 100 mg/ml, preferably 2 to 50 mg/ml, and more preferably 5 to 20 mg/ml.

In the present invention, a solution containing a protein and a gelling agent is added to an ionic cross-linking solution. It is preferred that the solution containing a protein and a gelling agent is added to the ionic cross-linking solution by dropping. By the dropping, particles of gel encapsulating the protein are formed. The volume of the solution containing a protein and a gelling agent to be added is not particularly limited. For example, the volume is 0.1 to 100 μl, preferably 2 to 50 μl, and more preferably 5 to 20 μl. The initial size of the formed particle has an average particle size of about 0.01 mm to about 10 mm, preferably about 1 mm to about 8 mm, and more preferably about 2 mm to 4 mm. Alternatively, in the case of micro-dispensation, the volume of the solution may be a small amount from 0.5 to 1.0 μl, and the average particle size may be from about 0.5 mm to about 0.9 mm.

The capsule for protein crystallization obtained by the present invention can be produced in one step. Thus, setup for crystallization is extremely easy, and it is convenient for micro-dispensation, crystallization condition screening, and automation. Moreover, there is no need to purchase an expensive crystallization plate. Also, transportation of the capsule is possible because the capsule resists mechanical shock.

The present invention provides a method for producing a protein crystal comprising maintaining the capsule formed as described above in a crystallization solution.

As used herein, a crystallization solution refers to a solution having a composition suitable for crystallization of a protein contained in the crystallization solution.

As for the crystallization solution, any known solution may be used, and a person skilled in the art can choose a suitable solution depending on the type of the protein. In one embodiment, the crystallization solution is an aqueous solution. The crystallization solution contains a buffer that comprises a precipitant. Examples of the precipitant include isopropanol, 2-methyl-2,4-pentane diol, Jeffamine M-600, polyethylene glycol (PEG) 400, polyethylene glycol (PEG) 4000, and polyethylene glycol (PEG) 8000. The concentration of the precipitant in the crystallization solution is about 1 to about 50% (v/v), preferably about 5 to about 40% (v/v). Examples of the buffer include an acetate buffer, MES (2-morpholino ethane sulfonic acid monohydrate) buffer, HEPES buffer, and bicine buffer. The concentration of the buffer in the crystallization solution is about 0.01 M to about 1 M, preferably about 0.1 M to about 0.5 M. The pH of the crystallization reagent is about 3.5 to about 9.5, preferably about 4.6 to about 9.0, although it depends on the type of buffer.

The crystallization solution may optionally contain a sodium salt or an ammonium salt. Examples of the sodium salt or the ammonium salt include sodium chloride, sodium formate, and ammonium chloride. The concentration of the salt in the crystallization solution is about 0.1 M to about 5.0 M, preferably about 0.4 M to about 3.5 M. Addition of a sodium ion such as sodium chloride to the crystallization reagent prevents the particle from deforming and facilitates formation of a small particle.

Although it is possible to transfer the capsule to the crystallization solution after the formation of the capsule, it is advantageous in terms of easy operation to use the ionic cross-linking solution as it is as the crystallization solution. In this case, for example, a conventional crystallization solution to which calcium is added may be used as both the ionic cross-linking solution and the crystallization solution.

As used herein, a non-volatile oil refers to an oily fluid that has a property to be separated from the crystallization solution without being mixed therewith, has a lower specific gravity than the crystallization solution, and serves to suppress the evaporation, or decrease the evaporation rate, of the crystallization solution by covering the surface thereof when the non-volatile oil is added to the crystallization solution.

As used herein, covering of the crystallization solution by the non-volatile oil means that the non-volatile oil covers the crystallization solution such that the non-volatile oil covers the entire surface of the crystallization solution which constitutes the lower layer. Although the thickness of the non-volatile oil varies depending on the amount of the crystallization solution, the size of the capsule and the like, the thickness needs to be great enough to enable addition of the capsule for protein crystallization into the non-volatile oil. If the non-volatile oil is so thin that the capsule for protein crystallization contacts the crystallization solution which constitutes the lower layer, undesirable ionic cross-linkage unintentionally proceeds at the tip end of the dispensing tip. In one embodiment, the thickness of the non-volatile oil with respect to 1 µl of the crystallization solution is preferably 2 to 3 mm.

The present invention provides a kit for producing a capsule for protein crystallization comprising a gelling agent and an ionic cross-linking solution, as well as a crystallization solution, a non-volatile oil, and a plate having one or more wells for placing the crystallization solution and the non-volatile oil therein. The ionic cross-linking solution and the crystallization solution may be identical to or different from each other. When the ionic cross-linking solution and the crystallization solution are identical to each other, the capsule can be left as it is for crystallization after the formation of the ionically cross-linked gel capsule.

The plate may be a commercially available crystallization plate. The well of the plate may be sealed with a removable film to prevent evaporation or contamination. In addition, a lid for preventing dust contamination may be attached to the plate after sealing. By dispensing the crystallization solution to the plate with a dispensing device such as a pipette manually or with an automatic dispensing device to prepare beforehand a plate in which the crystallization solution and the non-volatile oil covering the solution are placed therein, crystallization can be performed immediately as needed. A plate adapted to an automatic dispensing device is preferably a plate that conforms to the SBS (Society for Biomolecular Screening) standard. Examples of such a plate include the IMP@CT™ plate from Greiner. The film for sealing the plate is preferably a polyolefin film to which a silicon-based adhesive is attached. Examples of such a film include a Clear Sealing Film™ (Product No. HR4-521, Hampton Research Corp.).

In one embodiment, a kit further comprises a non-volatile oil. The non-volatile oil prevents the solution containing a protein and a gelling agent from attaching to the tip end of a dispensing device, e.g., to the tip, at the time of dispensation of the solution to a plate. In using such a kit, a user only has to mix the protein with the gelling agent, add the non-volatile oil, and dispense the mixture to the plate.

The present invention provides a plate for protein crystallization having a plurality of wells, wherein a crystallization solution containing a calcium ion (which is an ionic cross-linking solution), and a non-volatile oil covering the crystallization solution are placed in each well. With such a plate, a plurality of protein samples can be encapsulated and crystallized with ease and rapidity.

An example of preferred embodiments of the present invention will be described below with reference to the drawings.

In FIGS. 1A to D, sodium alginate is used as a gelling agent and a calcium-containing crystallization solution is used as an ionic cross-linking solution and a crystallization solution.

Figure 1:
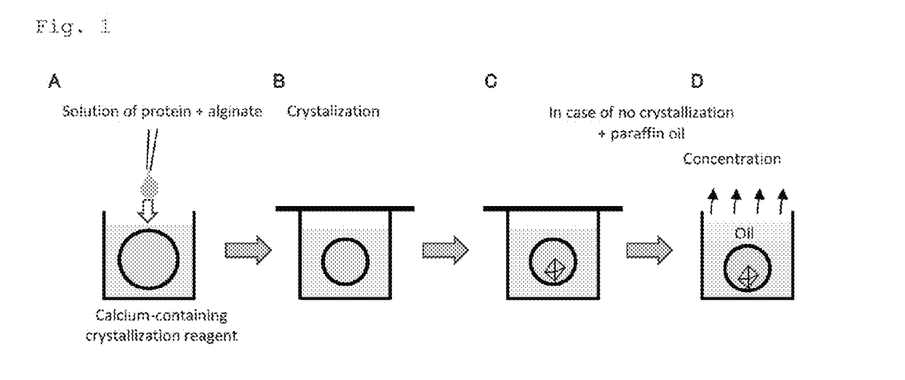
FIG. 1 schematically illustrates an aspect of procedure for capsule production and crystallization.

By adding the solution containing a protein and alginate to the calcium-containing crystallization solution dropwise, particles of calcium alginate are formed (FIG. 1A). By adding a sodium ion such as sodium chloride to the solution of sodium alginate beforehand, the viscosity of the solution is lowered to facilitate the dropping of the solution. The shape of the particles is usually spherical or near-spherical (for example, ellipsoidal). However, particles of other shapes may be formed depending on the aspect of dropping.

By allowing the resultant particles to stand with a lid put thereon, the protein is crystallized. When the concentration of calcium in the calcium-containing crystallization solution is higher than that of the solution containing a protein and alginate, a solvent in the particles is released from the particles due to the difference in osmotic pressure, and the particles shrink as ionic cross-linkage proceeds (FIG. 1B). In such a situation, the concentration of the protein in the particle increases to reach the condition where the crystallization is facilitated (FIG. 1C).

If crystallization does not occur under the above conditions, the lid of the container containing the calcium-containing crystallization solution is removed and a non-volatile oil such as paraffin oil, silicone oil, or a combination thereof is added over the calcium-containing crystallization solution to form a membrane of oil (FIG. 1D). Since the solvent is gradually released through this membrane, the concentration of the protein in the particle and the concentration of the crystallization reagent are increased further. Then, crystallization of the protein occurs.

Figure 2:
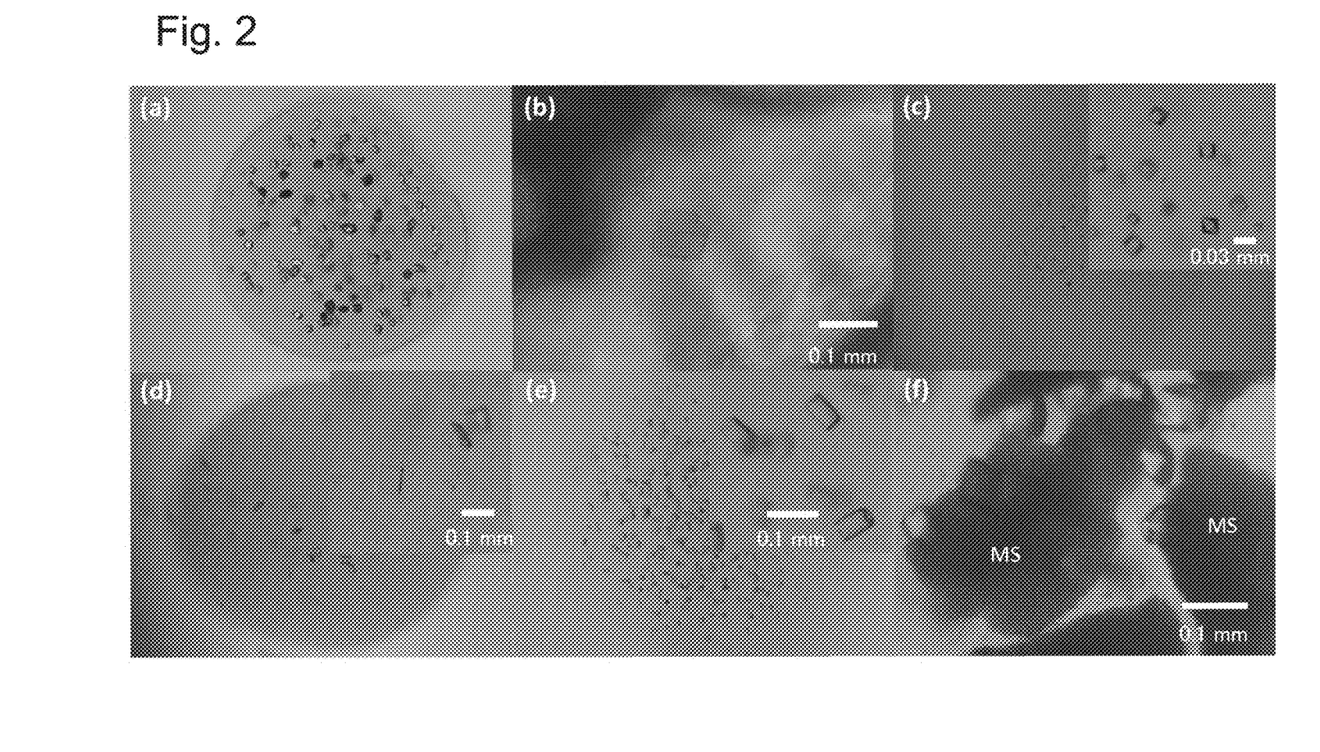
FIG. 2 shows photographs depicting protein crystallized in the capsules: (A) lysozyme from chicken egg white, (B) xylanase from *Trichoderma longibrachiatum*, (C) diphthine synthase from *Pyrococcus horikoshii* OT3 (protein ID70067, Y175H), (D) probable α-ribazole-5'-phosphate phosphatase from *Thermus thermophilus* HB8 (protein ID00367), (E) glucose-1-phosphate thymidylyltransferase from *Thermus thermophilus* HB8 (protein ID00403), and (F) a protein crystallized from a molecular sieve (MS) introduced into the capsule. The diameters of all the capsules are approximately 3 mm.

If zeolite is added to the solution containing a protein and a gelling agent beforehand, zeolite particles are encapsulated in the gel particles such that the zeolite particles can facilitate crystallization of the protein (FIG. 2F, Japanese Laid-open Patent Publication No. 2007-055931). Zeolite is a porous crystal comprising aluminum and silicon as main components. Zeolite includes natural zeolite and synthetic zeolite. Although both natural zeolite and synthetic zeolite may be used for the present invention, synthetic zeolite is preferred in terms of the variety of types, uniform composition and shape, and good reproducibility of results.

The type, property, shape and the like of zeolite are not particularly limited, and various zeolites may be used depending on factors such as the type of protein, desired shape of crystal, and space group. A typical example of synthetic zeolite is a molecular sieve (MS). A molecular sieve is a material having adsorption properties similar to those of natural zeolite and is used to adsorb various molecules. In addition, since a molecular sieve can be synthetically obtained, molecular sieves having various properties and shapes are manufactured. For example, there are molecular sieves of types 3A, 4A, 5A, 13X and the like (pore size increasing in this order), which are commercially available.

Figure 3:
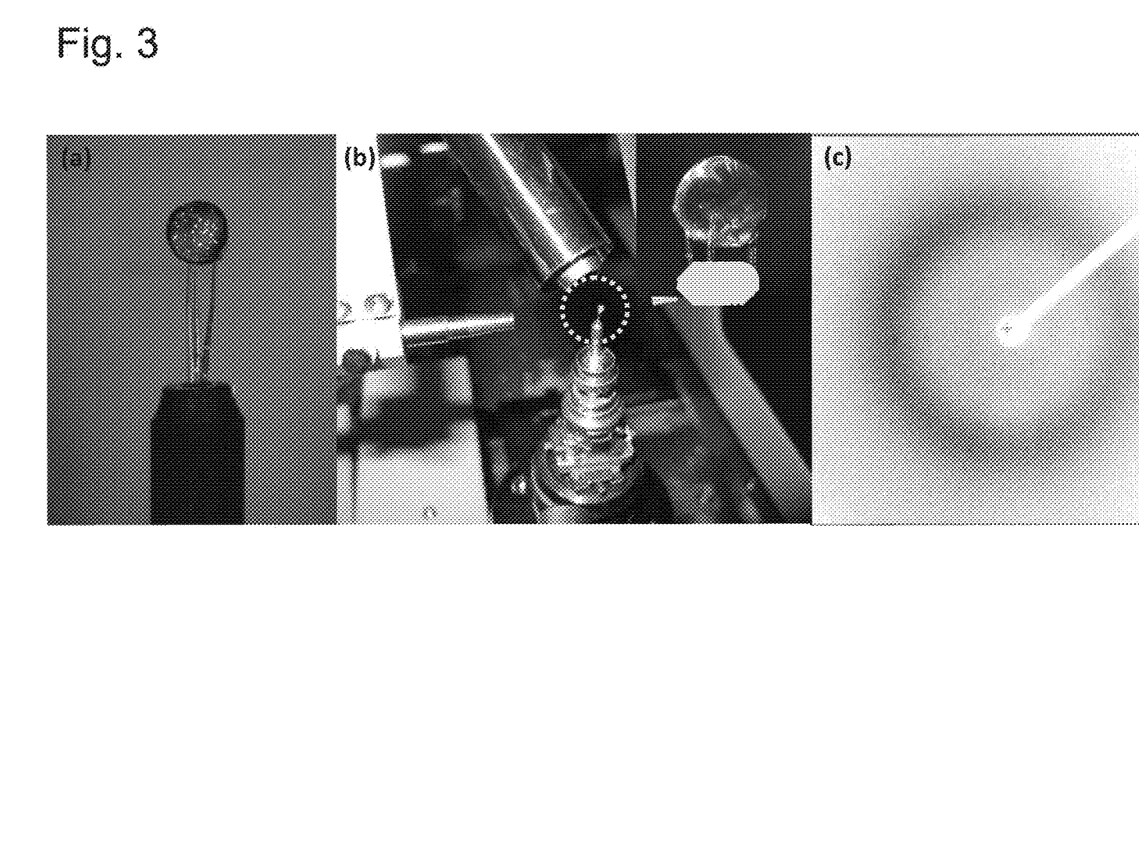
FIG. 3 illustrates a capsule containing a protein crystal mounted onto a diffractometer (A and B) and a diffraction image (C).

A crystal formed within the gel can be taken out together with the gel particle by any means such as a commercially available mounting device and be mounted onto an X-ray diffractometer. Thus, damage to the protein crystal is prevented (FIGS. 3A to C).

Figure 4:
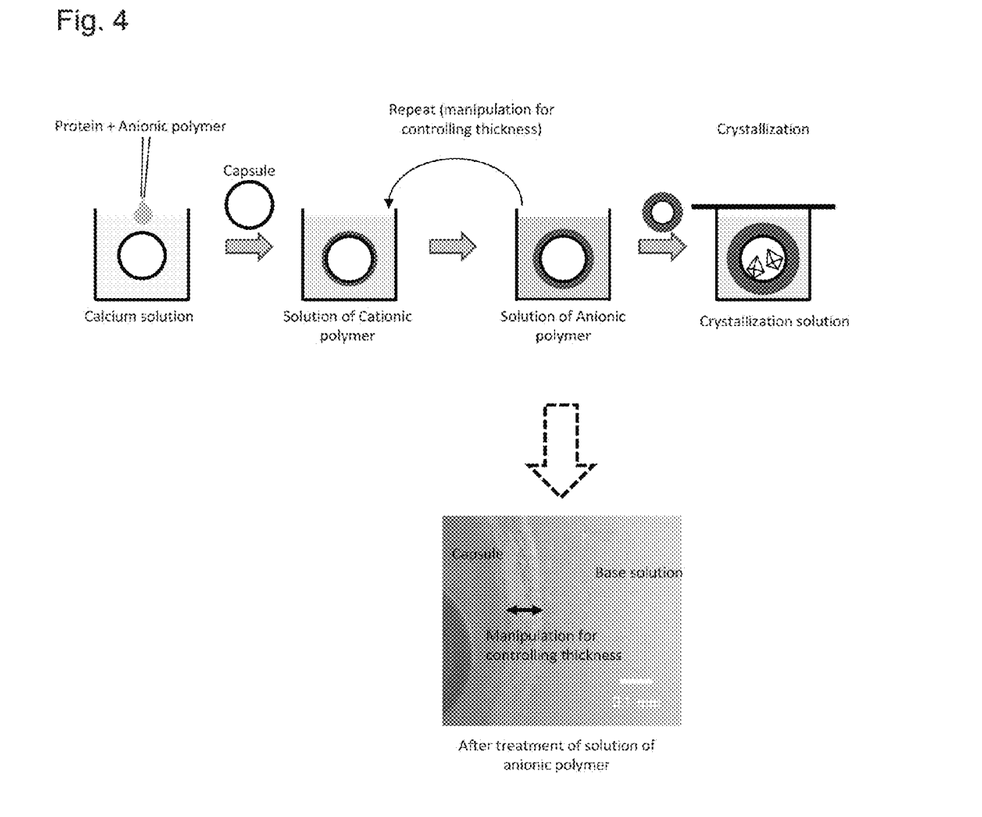
FIG. 4 schematically illustrates an aspect of procedure for producing a polymer capsule with polyion complex and crystallization.

In one embodiment of the present invention, a solution containing a protein and a gelling agent (anionic polymer) is added to an ionic cross-linking solution dropwise to form particles as described above, the particles are alternately immersed in a solution of a cationic polymer and in a solution of the anionic polymer to form a cover layer which is composed of the cationic polymer and the anionic polymer, and then the steps of crystallization similar to those in FIGS. 1B to D may be conducted (FIG. 4). This method is effective in controlling the membrane thickness to prevent the protein from flowing out of the capsule, and in avoiding rapid inflow of the crystallization solution into the capsule. This method is also useful, for example, when a crystallization solution having a high concentration of calcium ions is an obstacle to crystallization of a protein.

The anionic polymer includes the above-mentioned gelling agent (such as alginate), alginic acid, hyaluronic acid, N-acetylneuraminic acid, oxidized starch, dextran sulfate, chondroitin sulfate, heparin, and carboxymethylcellulose. The cationic polymer includes chitosan, polylysine, and polyethylene imine. The membrane thickness is about 50 μm to about 200 μm.

Although water is usually used as a solvent, a water-miscible solvent such as ethanol, methanol, isopropanol, DMF, THF, DMSO, dimethylacetamide, acetone, dioxane, ethylene glycol, propylene glycol, butylene glycol, and glycerol may be used alone, or two or more of them may be used as a mixture. Although it is preferred that such a solvent is mixed with water, it can be used in a nonaqueous system.

According to a method for producing a protein crystal of the present invention, a highly viscous gelling agent (for example, alginate) in a capsule suppresses convection of a solution containing a protein and also prevents sedimentation of a crystal. Thus, a high-quality crystal can be obtained.

According to a method for producing a protein crystal of the present invention, the concentrations of components in a capsule increase as time passes. By covering the surface of a crystallization solution with an oil (for example, paraffin oil), the concentrations of the components can be increased to extremes. Thus, according to the method of the present invention, a wide range of concentrations can be covered.

The protein crystal obtained by the present invention can be used for any application in which use of a protein crystal is desired. Examples of such application include, but are not limited to, structural analysis of the protein. For example, a protein crystal may be used for manufacturing a medical drug or a reagent.

The present invention provides a method for analyzing protein crystal structure comprising subjecting a protein crystal in an ionically cross-linked gel capsule produced as described above to protein structural analysis.

The method for analyzing a protein structure is not limited, but preferably an X-ray diffraction is used. Since a protein crystal obtained by the method of the present invention is present in a capsule, the diffraction resolution can be evaluated without directly touching the crystal. Further, treatment of a crystal such as a cryoprotectant and introduction of a heavy atom can be performed with ease.

As described above, a capsule for protein crystallization obtained by the present invention is suitable for automation, and so the present invention is useful when crystallization and structural analysis are to be automated.

Disclosures of all patents, patent applications, and literatures cited in this application are herein incorporated by reference in their entirety.

EXAMPLES

Example 1

Production of a Capsule Containing a Protein Crystal and X-Ray Diffraction Experiment For production of polymer capsules utilizing ionic cross-linkage and crystallization, a method for producing capsules by ionic cross-linkage of alginate with a calcium ion was performed (FIGS. 1A to D). In the procedure, 12 μl of a 5- to 20-mg/ml protein solution containing 1% sodium alginate was added dropwise to 500 μl of 0.2 M $CaCl_2$-containing crystallization reagent to produce capsules. As a result, five types of proteins ((a) lysozyme from chicken egg white, (b) xylanase from *Trichoderma longibrachiatum*, (c) diphthine synthase from *Pyrococcus horikoshii* OT3 (protein ID70067, Y175H), (d) α-ribazole-5'-phosphate phosphatase from *Thermus thermophilus* HB8 (protein ID00367), and (e) glucose-1-phosphate thymidylyltransferase from *Thermus thermophilus* HB8 (protein ID00403)) were crystallized successfully (FIGS. 2A to E).

The compositions of 0.2 M $CaCl_2$-containing crystallization reagent used for crystallization of the five types of proteins (a)-(e) were as follows:
(a) lysozyme: 5% (w/v) PEG 4000, 3.0 M NaCl, 0.2 M $CaCl_2$, 0.1 M HEPES (pH 7.5), (b) xylanase: 45% (v/v)-2-methyl-2,4-pentane diol, 0.2 M CaCl$_2$, 0.1 M BIS-TRIS (pH 6.5),
(c) ID70067: 3.5 M sodium formate, 0.2 M CaCl$_2$, 0.1 M MES (pH 6.5),
(d) ID00367: 3.0 M sodium chloride, 0.2 M CaCl$_2$, 0.1 M MES (pH 5.8), and
(e) ID00403: 3.5 M sodium formate, 0.2 M CaCl$_2$, 0.1 M HEPES (pH 7.5).

Further, protein crystallization using a synthetic zeolite that facilitates protein crystallization, molecular sieve (MS), was also conducted (FIG. 2F). A mixture of equal amounts (by weight) of molecular sieves 3A, 4A, 5A and 13X was used at a ratio of 5 mg/ml in a solution containing sodium alginate and a protein.

The resultant capsule containing a protein crystal was directly mounted onto a diffractometer (CuKα, Rigaku Corporation), and an X-ray diffraction experiment was conducted under the temperature condition of 100 K (FIGS. 3A to C). As a result, diffraction data were successfully collected at a resolution of 2.1 Å (Table 1).

TABLE 1

Result of Diffraction Experiment
The values in parenthesis are the values for a shell having the highest resolution.

| | |
|---|---|
| Space group | P4$_3$2$_1$2 |
| Lattice constant | a = b = 78.55, c = 37.18 |
| Measured wavelength (Å) | 1.000 |
| Resolution (Å) | 20-2.1 (2.17-2.10) |
| Number of unique reflections measured | 7154 (709) |
| R$_{merge}$ (%) | 16.9 (54.0) |
| Completeness (%) | 100 (100) |
| <I/σ(I)> | 5.5 (5.2) |
| Mosaicity (°) | 0.25 |

Example 2

Production of a Capsule Containing a Protein Crystal with Micro-Dispensation and X-Ray Diffraction Experiment Protein Crystallization In this study, more practical protein crystallization with micro-dispensation (0.5 to 1.0 μl of protein solution) and an X-ray diffraction experiment were conducted.

Figure 5:
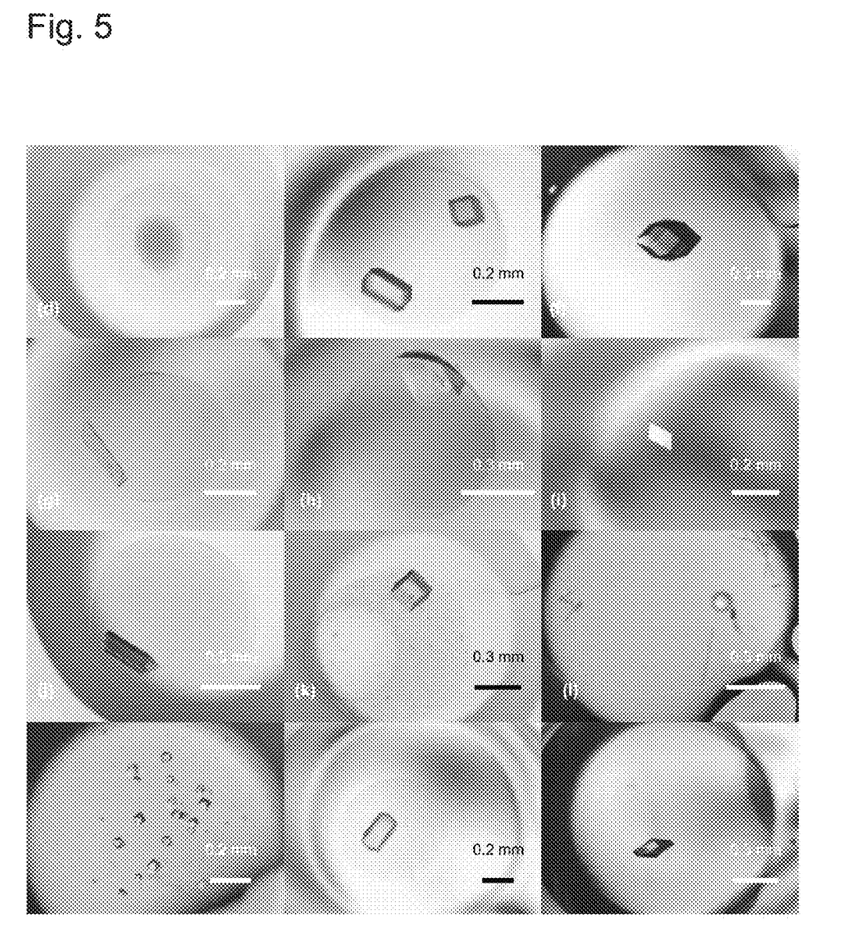

First, 1.0 μl of a crystallization reagent was dispensed using a dispensing device into a well of a crystallization plate (NUNC 72-well HLA plate). In this regard, to avoid interference with capsule production, contaminated air bubbles were removed. 70 kinds of Ca-containing crystallization reagents were dispensed to the crystallization plate. Compositions of the reagents are shown in Table 2. Next, the crystallization reagent drop was covered with a total of 15-20 μl paraffin oil. Before the sample was dispensed, paraffin oil was added to a mixed solution of a protein and alginate (aqueous solution of several milligrams of a protein, about 20 mM buffer (for lysozyme: acetate buffer (pH 4.6); for glucose isomerase: HEPES buffer (pH 7.4); for xylanase: Na/K phosphate buffer (pH 7); for catalase: commercially available catalase-containing buffer; for ID00367, ID00403, and ID70067: Tris buffer (pH 8.0)), 1% alginate, and 0.4 M sodium chloride). This paraffin oil serves to prevent a sample solution from attaching to the tip end of the dispensing tip. For the dispensation of 1.0 μl each of the protein solution, a total of about 30 μl paraffin oil was added to about 72 μl of a sample. 0.5 μl or 1.0 μl of the protein solution was injected into the oil layer of the crystallization reagent with the paraffin oil added thereupon. The drop sank into the layer of the crystallization reagent in about one minute. Ionic cross-linkage started immediately after the sinking and completed in several hours. After several days, protein were crystallized even with small amounts of the sample (FIGS. 5A to L). The proteins used were the same as those of Example 1.

In this experiment, protein crystallization was successfully made at the microscale.

TABLE 2

Compositions of 70 kinds of Ca-containing crystallization reagents

| No. | Precipitant | Salt | Cation | Buffer | pH | Reagent No. |
|---|---|---|---|---|---|---|
| 1 | 10% (v/v) isopropanol | | 0.2M CaCl$_2$ | 0.1M acetate | 4.6 | 1 |
| 2 | 10% (v/v) isopropanol | | 0.2M CaCl$_2$ | 0.1M MES | 5.8 | 2 |
| 3 | 10% (v/v) isopropanol | | 0.2M CaCl$_2$ | 0.1M MES | 6.5 | 3 |
| 4 | 10% (v/v) isopropanol | | 0.2M CaCl$_2$ | 0.1M HEPES | 7.5 | 4 |
| 5 | 10% (v/v) isopropanol | | 0.2M CaCl$_2$ | 0.1M bicine | 9.0 | 5 |
| 6 | 40% (v/v) 2-methyl-2,4-pentane diol | | 0.2M CaCl$_2$ | 0.1M acetate | 4.6 | 6 |
| 7 | 40% (v/v) 2-methyl-2,4-pentane diol | | 0.2M CaCl$_2$ | 0.1M MES | 5.8 | 7 |
| 8 | 40% (v/v) 2-methyl-2,4-pentane diol | | 0.2M CaCl$_2$ | 0.1M MES | 6.5 | 8 |
| 9 | 40% (v/v) 2-methyl-2,4-pentane diol | | 0.2M CaCl$_2$ | 0.1M HEPES | 7.5 | 9 |
| 10 | 40% (v/v) 2-methyl-2,4-pentane diol | | 0.2M CaCl$_2$ | 0.1M bicine | 9.0 | 10 |
| 11 | 25% (v/v) Jeffamine M-600 | | 0.2M CaCl$_2$ | 0.1M acetate | 4.6 | 11 |
| 12 | 25% (v/v) Jeffamine M-600 | | 0.2M CaCl$_2$ | 0.1M MES | 5.8 | 12 |
| 13 | 25% (v/v) Jeffamine M-600 | | 0.2M CaCl$_2$ | 0.1M MES | 6.5 | 13 |
| 14 | 25% (v/v) Jeffamine M-600 | | 0.2M CaCl$_2$ | 0.1M HEPES | 7.5 | 14 |
| 15 | 25% (v/v) Jeffamine M-600 | | 0.2M CaCl$_2$ | 0.1M bicine | 9.0 | 15 |
| 16 | 15% (v/v) PEG 400 | | 0.2M CaCl$_2$ | 0.1M acetate | 4.6 | 16 |
| 17 | 15% (v/v) PEG 400 | | 0.2M CaCl$_2$ | 0.1M MES | 5.8 | 17 |
| 18 | 15% (v/v) PEG 400 | | 0.2M CaCl$_2$ | 0.1M MES | 6.5 | 18 |
| 19 | 15% (v/v) PEG 400 | | 0.2M CaCl$_2$ | 0.1M HEPES | 7.5 | 19 |
| 20 | 15% (v/v) PEG 400 | | 0.2M CaCl$_2$ | 0.1M bicine | 9.0 | 20 |
| 21 | 10% (v/v) PEG 4000 | | 0.2M CaCl$_2$ | 0.1M acetate | 4.6 | 21 |
| 22 | 10% (v/v) PEG 4000 | | 0.2M CaCl$_2$ | 0.1M MES | 5.8 | 22 |
| 23 | 10% (v/v) PEG 4000 | | 0.2M CaCl$_2$ | 0.1M MES | 6.5 | 23 |
| 24 | 10% (v/v) PEG 4000 | | 0.2M CaCl$_2$ | 0.1M HEPES | 7.5 | 24 |
| 25 | 10% (v/v) PEG 4000 | | 0.2M CaCl$_2$ | 0.1M bicine | 9.0 | 25 |
| 26 | 10% (v/v) PEG 8000 | | 0.2M CaCl$_2$ | 0.1M acetate | 4.6 | 26 |
| 27 | 10% (v/v) PEG 8000 | | 0.2M CaCl$_2$ | 0.1M MES | 5.8 | 27 |

TABLE 2-continued

Compositions of 70 kinds of Ca-containing crystallization reagents

| No. | Precipitant | Salt | Cation | Buffer | pH | Reagent No. |
|---|---|---|---|---|---|---|
| 28 | 10% (v/v) PEG 8000 | | 0.2M CaCl$_2$ | 0.1M MES | 6.5 | 28 |
| 29 | 10% (v/v) PEG 8000 | | 0.2M CaCl$_2$ | 0.1M HEPES | 7.5 | 29 |
| 30 | 10% (v/v) PEG 8000 | | 0.2M CaCl$_2$ | 0.1M bicine | 9.0 | 30 |
| 31 | 10% (v/v) 2-methyl-2,4-pentane diol | 1.5M sodium chloride | 0.2M CaCl$_2$ | 0.1M acetate | 4.6 | 31 |
| 32 | 10% (v/v) 2-methyl-2,4-pentane diol | 1.5M sodium chloride | 0.2M CaCl$_2$ | 0.1M MES | 5.8 | 32 |
| 33 | 10% (v/v) 2-methyl-2,4-pentane diol | 1.5M sodium chloride | 0.2M CaCl$_2$ | 0.1M MES | 6.5 | 33 |
| 34 | 10% (v/v) 2-methyl-2,4-pentane diol | 1.5M sodium chloride | 0.2M CaCl$_2$ | 0.1M HEPES | 7.5 | 34 |
| 35 | 10% (v/v) 2-methyl-2,4-pentane diol | 1.5M sodium chloride | 0.2M CaCl$_2$ | 0.1M bicine | 9.0 | 35 |
| 36 | 5% (v/v) Jeffamine M-600 | 0.4M sodium chloride | 0.2M CaCl$_2$ | 0.1M acetate | 4.6 | 36 |
| 37 | 5% (v/v) Jeffamine M-600 | 0.4M sodium chloride | 0.2M CaCl$_2$ | 0.1M MES | 5.8 | 37 |
| 38 | 5% (v/v) Jeffamine M-600 | 0.4M sodium chloride | 0.2M CaCl$_2$ | 0.1M MES | 6.5 | 38 |
| 39 | 5% (v/v) Jeffamine M-600 | 0.4M sodium chloride | 0.2M CaCl$_2$ | 0.1M HEPES | 7.5 | 39 |
| 40 | 5% (v/v) Jeffamine M-600 | 0.4M sodium chloride | 0.2M CaCl$_2$ | 0.1M bicine | 9.0 | 40 |
| 41 | 10% (v/v) PEG 400 | 3.0M sodium chloride | 0.2M CaCl$_2$ | 0.1M acetate | 4.6 | 41 |
| 42 | 10% (v/v) PEG 400 | 3.0M sodium chloride | 0.2M CaCl$_2$ | 0.1M MES | 5.8 | 42 |
| 43 | 10% (v/v) PEG 400 | 3.0M sodium chloride | 0.2M CaCl$_2$ | 0.1M MES | 6.5 | 43 |
| 44 | 10% (v/v) PEG 400 | 3.0M sodium chloride | 0.2M CaCl$_2$ | 0.1M HEPES | 7.5 | 44 |
| 45 | 10% (v/v) PEG 400 | 3.0M sodium chloride | 0.2M CaCl$_2$ | 0.1M bicine | 9.0 | 45 |
| 46 | 5% (v/v) PEG 4000 | 3.0M sodium chloride | 0.2M CaCl$_2$ | 0.1M acetate | 4.6 | 46 |
| 47 | 5% (v/v) PEG 4000 | 3.0M sodium chloride | 0.2M CaCl$_2$ | 0.1M MES | 5.8 | 47 |
| 48 | 5% (v/v) PEG 4000 | 3.0M sodium chloride | 0.2M CaCl$_2$ | 0.1M MES | 6.5 | 48 |
| 49 | 5% (v/v) PEG 4000 | 3.0M sodium chloride | 0.2M CaCl$_2$ | 0.1M HEPES | 7.5 | 49 |
| 50 | 5% (v/v) PEG 4000 | 3.0M sodium chloride | 0.2M CaCl$_2$ | 0.1M bicine | 9.0 | 50 |
| 51 | 5% (v/v) PEG 8000 | 3.0M sodium chloride | 0.2M CaCl$_2$ | 0.1M acetate | 4.6 | 51 |
| 52 | 5% (v/v) PEG 8000 | 3.0M sodium chloride | 0.2M CaCl$_2$ | 0.1M MES | 5.8 | 52 |
| 53 | 5% (v/v) PEG 8000 | 3.0M sodium chloride | 0.2M CaCl$_2$ | 0.1M MES | 6.5 | 53 |
| 54 | 5% (v/v) PEG 8000 | 3.0M sodium chloride | 0.2M CaCl$_2$ | 0.1M HEPES | 7.5 | 54 |
| 55 | 5% (v/v) PEG 8000 | 3.0M sodium chloride | 0.2M CaCl$_2$ | 0.1M bicine | 9.0 | 55 |
| 56 | | 3.0M sodium chloride | 0.2M CaCl$_2$ | 0.1M acetate | 4.6 | 56 |
| 57 | | 3.0M sodium chloride | 0.2M CaCl$_2$ | 0.1M MES | 5.8 | 57 |
| 58 | | 3.0M sodium chloride | 0.2M CaCl$_2$ | 0.1M MES | 6.5 | 58 |
| 59 | | 3.0M sodium chloride | 0.2M CaCl$_2$ | 0.1M HEPES | 7.5 | 59 |
| 60 | | 3.0M sodium chloride | 0.2M CaCl$_2$ | 0.1M bicine | 9.0 | 60 |
| 61 | | 3.5M sodium formate | 0.2M CaCl$_2$ | 0.1M acetate | 4.6 | 61 |
| 62 | | 3.5M sodium formate | 0.2M CaCl$_2$ | 0.1M MES | 5.8 | 62 |
| 63 | | 3.5M sodium formate | 0.2M CaCl$_2$ | 0.1M MES | 6.5 | 63 |
| 64 | | 3.5M sodium formate | 0.2M CaCl$_2$ | 0.1M HEPES | 7.5 | 64 |
| 65 | | 3.5M sodium formate | 0.2M CaCl$_2$ | 0.1M bicine | 9.0 | 65 |
| 66 | | 1.7M ammonium chloride | 0.2M CaCl$_2$ | 0.1M acetate | 4.6 | 66 |
| 67 | | 1.7M ammonium chloride | 0.2M CaCl$_2$ | 0.1M MES | 5.8 | 67 |
| 68 | | 1.7M ammonium chloride | 0.2M CaCl$_2$ | 0.1M MES | 6.5 | 68 |
| 69 | | 1.7M ammonium chloride | 0.2M CaCl$_2$ | 0.1M HEPES | 7.5 | 69 |
| 70 | | 1.7M ammonium chloride | 0.2M CaCl$_2$ | 0.1M bicine | 9.0 | 70 |

An X-ray diffraction experiment on a crystal crystallized in the capsule for X-ray diffraction experiment was conducted with the following procedure.

Figure 6:
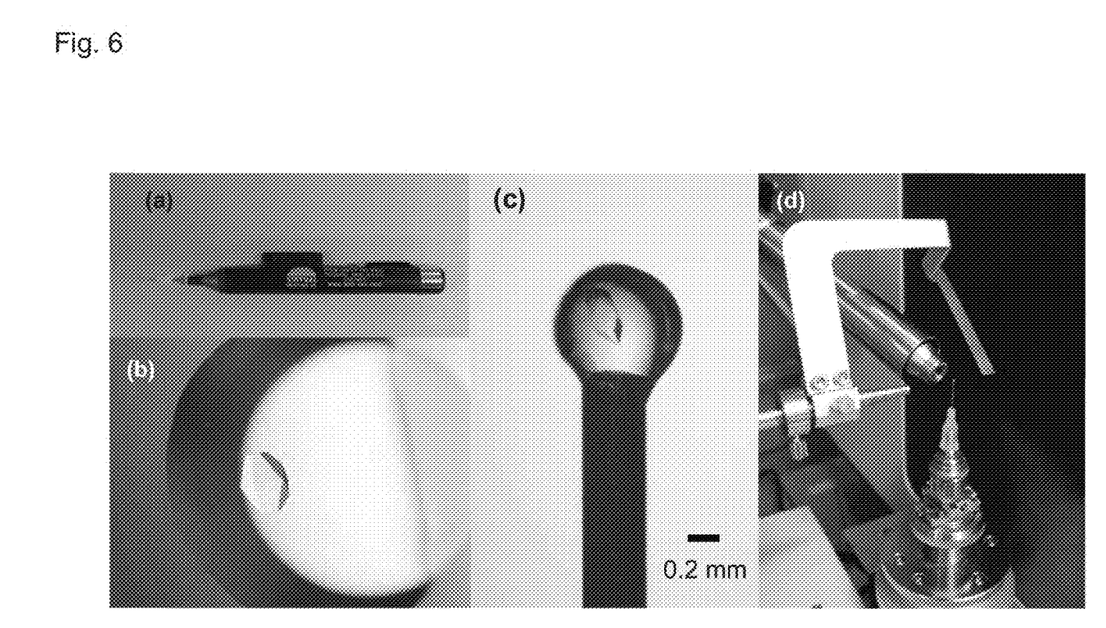
FIG. 6 shows (A) a photograph of vacuum tweezers to which a tip for the vacuum tweezers is attached, (B) a crystal of lysozyme, (C) treatment of a protein crystal with a cryoprotectant, and (D) a photograph of mounting of a capsule onto a diffractometer.

A tip for vacuum tweezers (ST-C series, Miruc Optical Co., Ltd.) was attached to commercially available vacuum tweezers. A capsule was sucked to take out the crystal. FIG. 6A is a photograph of the vacuum tweezers to which the tip for vacuum tweezers was attached. FIG. 6B illustrates a crystal of lysozyme. Next, air was blown from the tweezers, and the capsule was sunk into a cryoprotectant solution (a crystallization reagent (3.0 M sodium chloride, 0.2 M CaCl$_2$, 0.1 M bicine (pH 9.0)) containing 30% (v/v) glycerol) and immersed fully to treat the protein crystal with the cryoprotectant (FIG. 6C). Then, the capsule was picked up, the tip was detached from the vacuum tweezers, and the tip was mounted onto a diffractometer. At that point, the flash cooling was performed under the temperature condition of 100 K (FIG. 6D), and diffraction data were collected using an in-house diffractometer. Consequently, the following set of diffraction data was obtained: space group: P43212; lattice constant: a=b=78.62, c=37.02 Å, diffraction resolution: 1.55 Å; and mosaicity: 0.33-0.39°.

In this diffraction experiment, utilization of vacuum tweezers makes the operations of cryoprotectant treatment and flush cooling easy. Thus, even researchers who are inexperienced in protein X-ray crystal structure analysis can easily conduct the experiment. In addition, the diffraction data can be collected without directly touching the protein crystal. This would be useful in constructing a fully automated system of structural analysis.

Example 3

Storage of a Capsule Containing a Protein Crystal in Liquid Nitrogen

In this Example, a procedure for storing the protein crystal in liquid nitrogen was established. This procedure is desirable to conduct X-ray crystal structural analysis.

Experimental Procedure

A washer (inside diameter×outside diameter, 5 mm×12 mm) was fitted to the body of a tip for vacuum tweezers used for an X-ray diffraction experiment (ST-C series, Miruc Optical Co., Ltd.). The tip for vacuum tweezers onto which a capsule containing a protein crystal had been mounted was grasped with a CryoTong (trademark) (21 mm, Hampton Research Corp.) that was cooled with liquid nitrogen under the temperature condition of 100 K. The CryoTong was engaged with the washer of the tip, and the tip was removed from the head of a goniometer. The CryoTong was vertically inverted, and the base of the tip was held with a clamp (Hampton Research Corp.) of which the ends had been processed so that the width conforms to the diameter of the tip. Then, the tip was removed from the CryoTong and put in a CryoCane (Hampton Research Corp.) in liquid nitrogen. Thus, the crystal was stored in liquid nitrogen in a vessel. When the crystal was mounted onto the head of the goniometer again, the reverse procedure was conducted.

Example 4

Comparison of Diffraction Data Before and After Storage in Liquid Nitrogen

In this Example, it was demonstrated that a capsule containing a protein crystal can be reliably stored in accordance with the procedure for storing a sample in liquid nitrogen in Example 3.

Experimental Procedure

A protein crystal was obtained by covering 0.5 μl of crystallization reagent (3.0 M sodium chloride, 0.2 M calcium chloride, and 0.1 M bicine buffer (pH 9.0)) with 15 μl of paraffin oil and dispensing 0.5 μl of a protein solution (20 mg/ml lysozyme, 10 mM acetate buffer (pH 4.6), 0.4 M sodium chloride, and 1(w/v) % alginate) into the oil layer to produce a capsule. Next, the capsule containing the protein crystal was immersed in a cryoprotectant solution (the crystallization reagent containing 35 (v/v) % glycerol) for 90 seconds. Then, flash cooling was performed under the cryostream at 100 K, the capsule was mounted onto a diffractometer, and diffraction data were collected (Diffraction Data 1). To collect diffraction data after storage, the capsule used in the diffraction experiment was stored in accordance with the procedure for storing in liquid nitrogen in Example 3. The sample stored in liquid nitrogen was mounted onto the diffractometer again, and diffraction data were collected (Diffraction Data 2).

The data of diffraction experiments were collected twice, i.e., before and after the storage in liquid nitrogen, and compared (Table 3). The results showed that the quality of diffraction data was almost the same before and after storage. The manipulation of storage in liquid nitrogen did not decrease the quality of the protein crystal severely. Thus, it was confirmed that in accordance with the procedure above, the sample can be stored stably without damaging it.

TABLE 3

Statistical information on diffraction data

| | Diffraction data 1 | Diffraction data 2 |
|---|---|---|
| Space group | P4₃2₁2 | P4₃2₁2 |
| Lattice constant a, b, c (Å) | 78.6, 78.6, 37.0 | 78.6, 78.6, 37.1 |
| Diffraction resolution (Å) | 20-1.50 (1.55-1.50) | 20-1.50 (1.55-1.50) |
| Number of independent reflections | 19189 (1881) | 19182 (1884) |
| Redundancy | 12.3 (10.2) | 12.4 (10.3) |

TABLE 3-continued

Statistical information on diffraction data

| | Diffraction data 1 | Diffraction data 2 |
|---|---|---|
| Completeness (%) | 100 (100) | 100 (100) |
| $R_{merge}$ (%) | 8.4 (51.8) | 7.2 (50.0) |
| <I/sigma(I)> | 8.3 (3.2) | 9.4 (3.7) |
| Mosaicity (°) | 0.35 | 0.35 |

The values in parenthesis are the values for a shell having the highest resolution.

The invention claimed is:

1. A method for producing a capsule for protein crystallization, comprising:
    adding a solution containing a protein and a gelling agent to an ionic cross-linking and crystallization solution, to thereby form an ionically cross-linked gel capsule,
    wherein the solution containing the protein and the gelling agent is added to the ionic cross-linking and crystallization solution by dropping,
    wherein the ionically cross-linked gel capsule is maintained in the ionic cross-linking and crystallization solution to thereby produce a protein crystal encapsulated within a shell of the ionically cross-linked gel capsule, and
    wherein the ionic cross-linking and crystallization solution comprises a buffer, a precipitant and a calcium ion, a concentration of the calcium ion in the ionic cross-linking and crystallization solution being higher than a concentration of a calcium ion in the solution containing the protein and the gelling agent.

2. A method for producing a protein crystal, comprising:
    adding a solution containing a protein and a gelling agent to an ionic cross-linking solution to form an ionically cross-linked gel capsule, the solution containing the protein and the gelling agent being added to the ionic cross-linking solution by dropping, the ionic cross-linking solution comprising a calcium ion;
    transferring the capsule to a crystallization solution, the crystallization solution comprising a buffer, a precipitant and a calcium ion, a concentration of the calcium ion in the crystallization solution being higher than a concentration of a calcium ion in the solution containing the protein and the gelling agent; and
    maintaining the capsule in the crystallization solution to produce a protein crystal encapsulated within a shell of the ionically cross-linked gel capsule.

3. A method for producing a protein crystal, comprising:
    providing a plate for protein crystallization, wherein the plate has one or more wells, and an ionic cross-linking and crystallization solution and a non-volatile oil covering the ionic cross-linking and crystallization solution are placed in each well; and
    adding a solution containing a protein and a gelling agent to the non-volatile oil to thereby form and maintain an ionically cross-linked gel capsule in the ionic cross-linking and crystallization solution, the ionically cross-linked gel capsule having a protein crystal encapsulated within a shell of the ionically cross-linked gel capsule,
    wherein the solution containing the protein and the gelling agent is added to the ionic cross-linking and crystallization solution by dropping, and
    wherein the ionic cross-linking and crystallization solution comprises a buffer, a precipitant and a calcium ion, a concentration of the calcium ion in the ionic cross-linking and crystallization solution being higher than a concentration of a calcium ion in the solution containing the protein and the gelling agent.

4. The method of claim 1, wherein the precipitant is at least one selected from the group consisting of isopropanol, 2-methyl-2,4-pentane diol, Jeffamine M-600, polyethylene glycol (PEG) 400, polyethylene glycol (PEG) 4000, and polyethylene glycol (PEG) 8000.

5. The method of claim 2, wherein the precipitant is at least one selected from the group consisting of isopropanol, 2-methyl-2,4-pentane diol, Jeffamine M-600, polyethylene glycol (PEG) 400, polyethylene glycol (PEG) 4000, and polyethylene glycol (PEG) 8000.

6. A method for producing a protein crystal, comprising:
providing a plate for protein crystallization, wherein the plate has one or more wells, and an ionic cross-linking solution and a non-volatile oil covering the ionic cross-linking solution are placed in each well, the ionic cross-linking solution comprising a calcium ion, adding a solution containing a protein and a gelling agent to the non-volatile oil by dropping, thereby forming an ionically cross-linked gel capsule in the ionic cross-linking solution, transferring the capsule to a crystallization solution, the crystallization solution comprising a buffer, a precipitant and a calcium ion, a concentration of the calcium ion in the crystallization solution being higher than a concentration of a calcium ion in the solution containing the protein and the gelling agent, and maintaining the capsule in the crystallization solution to produce a protein crystal encapsulated within a shell of the ionically cross-linked gel capsule.

7. The method of claim 3, wherein the precipitant is at least one selected from the group consisting of isopropanol, 2-methyl-2,4-pentane diol, Jeffamine M-600, polyethylene glycol (PEG) 400, polyethylene glycol (PEG) 4000, and polyethylene glycol (PEG) 8000.

8. The method of claim 6, wherein the precipitant is at least one selected from the group consisting of isopropanol, 2-methyl-2,4-pentane diol, Jeffamine M-600, polyethylene glycol (PEG) 400, polyethylene glycol (PEG) 4000, and polyethylene glycol (PEG) 8000.

\* \* \* \* \*